United States Patent [19]

Erb

[11] 4,245,623
[45] Jan. 20, 1981

[54] METHOD AND APPARATUS FOR THE HYSTEROSCOPIC NON-SURGICAL STERILIZATION OF FEMALES

[76] Inventor: Robert A. Erb, P.O. Box 86, Valley Forge, Pa. 19481

[21] Appl. No.: 913,066

[22] Filed: Jun. 6, 1978

[51] Int. Cl.³ .............................................. A61B 19/00
[52] U.S. Cl. ................................ 128/1 R; 128/303 R
[58] Field of Search ............ 128/1 R, 2 R, 130, 303 R, 128/234–236, 218 A

[56] References Cited

U.S. PATENT DOCUMENTS

| | | | |
|---|---|---|---|
| 2,627,270 | 2/1953 | Glass | 128/218 A |
| 3,422,813 | 1/1969 | Helmer et al. | 128/1 R |
| 3,472,226 | 10/1969 | Haber | 128/218 R |
| 3,707,146 | 12/1972 | Cook et al. | 128/246 X |
| 3,805,767 | 4/1974 | Erb | 128/1 R |
| 3,858,586 | 1/1975 | Lessen | 128/4 X |
| 3,870,072 | 3/1975 | Lindemann | 128/184 |
| 3,918,431 | 11/1975 | Sinnreich | 128/1 R |
| 4,132,231 | 1/1979 | Puccio | 128/218 A |
| 4,160,446 | 7/1979 | Barrington | 128/1 R |

OTHER PUBLICATIONS

Thompson et al.–Human Sterilization–1971, Charles C. Thomas (Pub.), Chap. X30, pp. 353–359.

*Primary Examiner*—Dalton L. Truluck
*Attorney, Agent, or Firm*—Hopgood, Calimafde, Kalil, Blaustein & Lieberman

[57] ABSTRACT

A method and apparatus is provided for the non-surgical, reversible sterilization of females. In the method of the invention an operation-channel hysteroscope is employed for optical guidance of an obturator tip into alignment with the uterine end of the oviduct. The obturating tip is carried upon the inner of two concentric tubes and a curable elastomer-precursor composition is injected through the inner tube, through an aperture in the obturating tip and into the oviduct in an amount sufficient to fill and mechanically lock to the oviduct portion adjacent to the uterus. The elastomeric composition is allowed to solidify in situ where it adheres to and becomes integral with the tip. Maintaining the outer tube in fixed position, the inner tube is then withdrawn, forcing the obturating tip to be ejected from the inner tube where it now remains integral with the resultant oviduct block. The foregoing procedure is then repeated for the opposing oviduct. The resultant blocks prevent the passage of ovum from the ovaries to the uterus and sperm from entering the oviduct, thereby preventing contraception. The oviduct blocks can, if desired, be removed non-surgically by utilizing an apparatus which grips the tip portion and extracts the block. An arrangement is also disclosed wherein the obturating tip is formed simultaneously with the oviduct block, eliminating the need for a separate tip.

26 Claims, 16 Drawing Figures

FIG. 3D GUIDE REMOVED

FIG. 3C RELEASE

FIG. 3B FLUID FLOW

FIG. 3A POSITIONING

FIG. 4E GUIDE REMOVED

FIG. 4D RELEASE

FIG. 4C RUPTURING ELASTOMER

FIG. 4B FLUID FLOW

FIG. 4A POSITIONING

METHOD AND APPARATUS FOR THE HYSTEROSCOPIC NON-SURGICAL STERILIZATION OF FEMALES

BACKGROUND OF THE INVENTION

This invention is concerned with a method and apparatus for the non-surgical, reversible sterilization of females and is related to my prior patent entitled METHOD AND APPARATUS FOR NON-SURGICAL REVERSIBLE STERILIZATION OF FEMALES filed Feb. 26, 1973, Ser. No. 33,813, issued Apr. 23, 1974 as U.S. Pat. No. 3,805,767 and re-issued on Aug. 9, 1977 as U.S. Pat. No. Re. 29,345.

In the field of birth control, contraception prevention methods are considerably more acceptable for controlling population growth than abortion. Each of the methods either conventionally available for contraception, or suggested for that purpose have had inherent limitations proscribing their overall applicability and effectiveness.

Ideally, any contraceptive method should be 100% effective in its prevention; should not interfere with sexual relationships; and should be low in cost, taking into consideration the effective life of the contraceptive. In addition, the contraceptive method should not embrace physiological, or psychological side-effects, and ideally should be reversible.

Devices such as condoms, diaphragms and vaginal foams are in general highly unreliable. Intra-uterine devices are limited in their application and often cause irritation, discomfort and heavy bleeding. They may also be rejected without the knowledge of the wearer, resulting in pregnancy. The contraceptive pill interferes with the normal hormone balance and as more about its side effects is learned its acceptability among potential users is diminished.

There are two methods in wide use today which are generally considered to be effective contraceptive methods. These are oviduct ligation (including electrocautery and rubber ring techniques) for females and vasectomies for males. In both of these methods the reproductive ducts are severed, or made discontinuous, and these techniques, if properly performed (and there is no natural regeneration) are 100% effective. Both methods, however, require surgery and both are difficult, if not impossible to reverse and restore normal reproductive capacity.

It has been well-established that a primary cause of infertility in females is blockage of the oviducts from the uterus. The ovum when discharged is absorbed by the body and is thereby prevented from coming in contact with the sperm, negating conception. Females having this natural condition normally do not even recognize its existence and there are no known side effects, aside from infertility. Accordingly, there have been numerous recent teachings of artificial methods and devices for blocking the oviduct to impart sterility. A sample of such teachings are referred to in my prior patent.

Suffice to say that none of the arrangements heretofore promulgated can be reversed without surgery. Those which are capable of non-surgical reversal are substantially less than 100% effective.

Accordingly it is the object of this invention to overcome deficiencies in conventional contraceptive techniques as aforementioned and provide a method and apparatus which is both non-surgical and reversible.

It is another object of this invention to provide a contraceptive method which is safe, consistently reliable, and relatively inexpensive.

It is another object of this invention to provide a reversible uterine block without the necessity of employing fluoroscopic techniques, but with similar reliability.

It is a still further object of this invention to satisfy the foregoing objects utilizing conventional operating hysteroscopes having a professional familiarity to gynecologists, and thereby greater acceptability and ease of use.

SUMMARY OF THE INVENTION

In accordance with the invention a method and apparatus is provided to form oviduct blocks or plugs which prevent conception and which when in place can be non-surgically removed. The apparatus includes a standard operating hysteroscope through which a pair of concentric tubes are inserted, the inner tube carrying an obturating tip. The obturating tip is visually aligned with the uterine end of the oviduct and mixture of fluid elastomer-precursor material and a catalyst for polymerizing the material is injected through an aperture in the tip, into the oviduct. The catalyzed elastomer-precursor material is allowed to solidify and adhere to the tip. The tip is released upon withdrawal of the inner tube (by the confining action of the outer tube) and remains integral with the cured elastomeric material to form the oviduct plug of the invention. The hysteroscope is then removed. The oviduct plug can be removed non-surgically by repositioning the same, or a similar, hysteroscope and employing a tip-grasping implement through the hysteroscope operating channel, removing the plug and thereby restoring fertility.

BRIEF DESCRIPTION OF THE DRAWINGS

FIG. 3A–3D illustrates schematically the steps in locating, forming and releasing the oviduct block.

FIG. 4A–4E schematically illustrates a series of steps similar to those shown in FIG. 3 in an alternate embodiment wherein the use of a distinct obturating tip is omitted.

DETAILED DESCRIPTION OF THE PREFERRED EMBODIMENTS OF THE INVENTION

As in my prior invention referred to above, the method of this invention provides an oviduct block formed in situ in the oviduct. The block is preferably formed from a medically inert polymer (elastomer) which has approximately the same modulus of elasticity as the oviduct, when cured. The selection of the proper modulus of elasticity for the cured plastic aids both in the preventing of expulsion and the elimination of physical discomfort.

A material which has been found most useful in the method of this invention is commercially available medical grade silicone elastomers, such as hydroxyl-end-blocked poly (dimethyl siloxane) which contains propyl orthosilicate as a cross-linking agent, and a silica filler (diatomaceous earth) at a concentration of 23% by weight. Upon mixing with tin (II) octoate the cross-linking proceeds with the splitting out of propanol without generation of sensible heat. Another such material is silphenylene polymer (which is similarly cured). It is suggested that there be incorporated within the composition a radiopaque material such as atomized spherical fine silver powder (minus 400 mesh) barium sulfate, or bismuth trioxide to permit x-ray visualization of the blocks (plugs) in place. Prior to cross-linking the block-forming composition preferably has incorporated therein a diluent to reduce viscosity (the described material has a viscosity of about 500 poise). A suitable diluent is an end-blocked poly (dimethyl siloxane) of about 0.2 poise viscosity.

The obturator tips are preferably prefabricated by molding. They are made of a material similar to the block or plug material described above, however excluding any diluent for viscosity reduction. The obturator tip is shown in detail in FIG. 2 at 20. The presentation face 21 is formed to interface as close as possible with the uterine end of the oviduct (see e.g., FIG. 3A). Channel 22 contained therein permits the passage of the curing elastomer-precursor fluid and may be flanged slightly outwardly at 25 to permit a mechanical (as well as integral) bond to the cured elastomeric material, e.g., as shown in FIGS. 3C and 3D. The internal dimension of the obturator tip is slightly less than the external dimension of the flow channel tube 30 upon which it rests (after being stretched slightly). Flash 23 on the obturating tip 20 is formed at the parting line during molding and is preferably permitted to remain since it augments the structural soundness of the tip during its stretching over the flow channel tube 30.

Figures 2, 5, 5A:
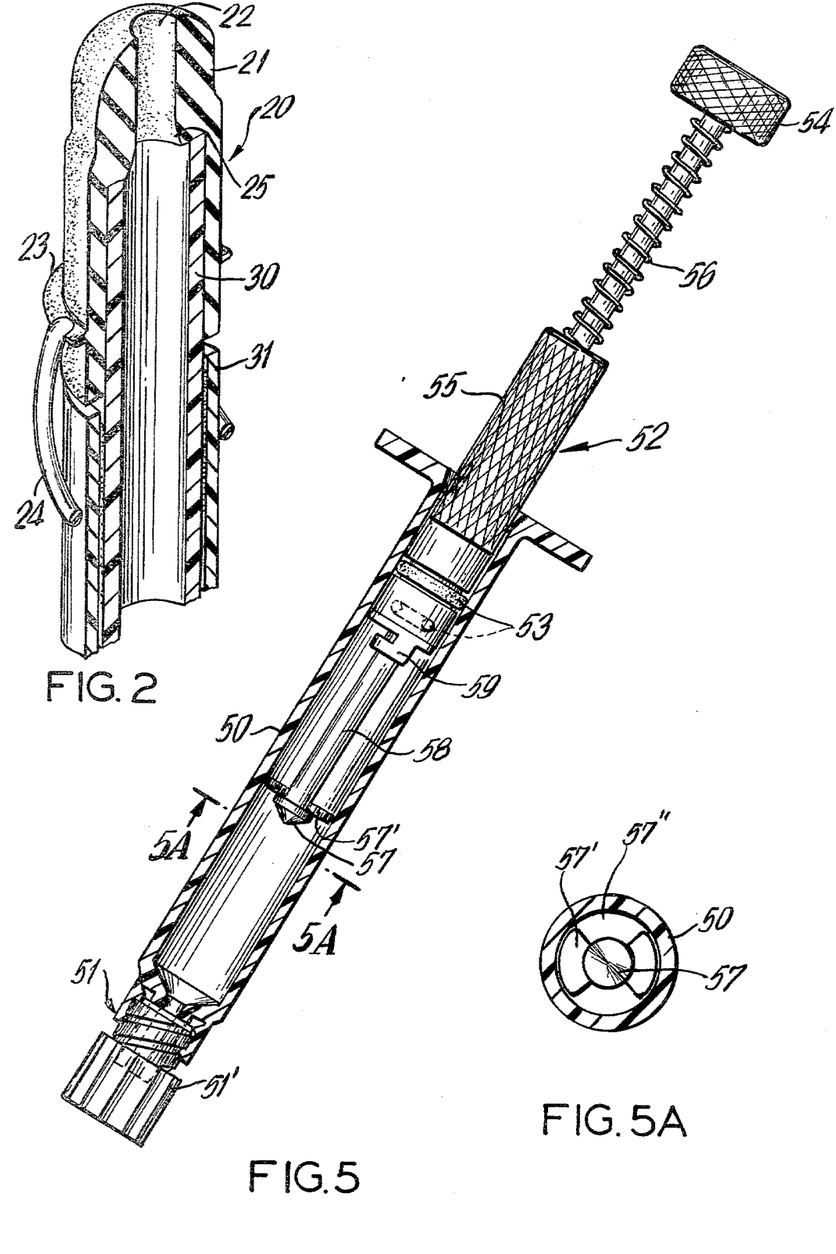
FIG. 2 is a detail of the obturating tip shown in relationship to the concentric tubes.
FIG. 5 and 5A illustrates a non-air-entraining mixer and dispenser used for both mixing and dispensing the elastomeric fluid material and catalyst.
Figure 3A:
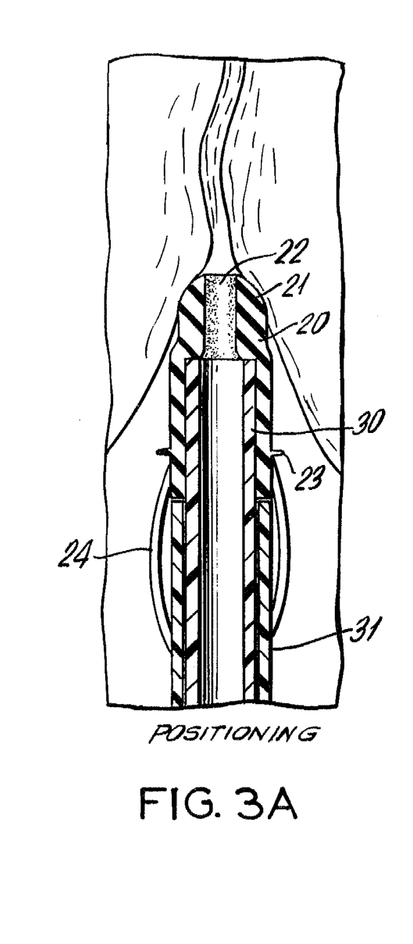
Figure 3B:
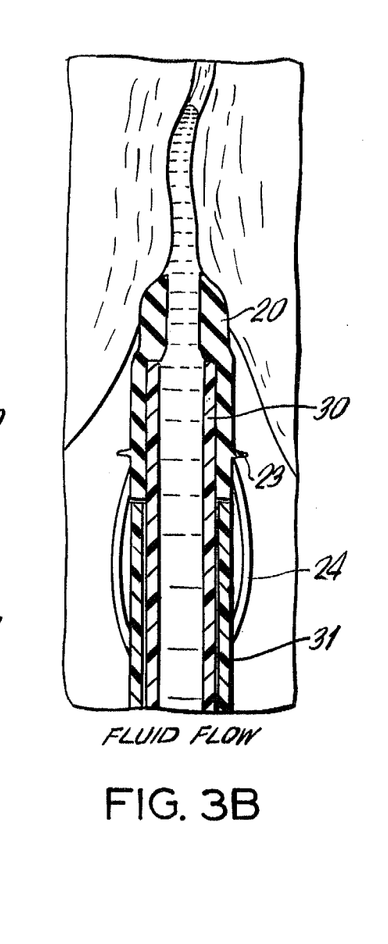
Figure 3C:
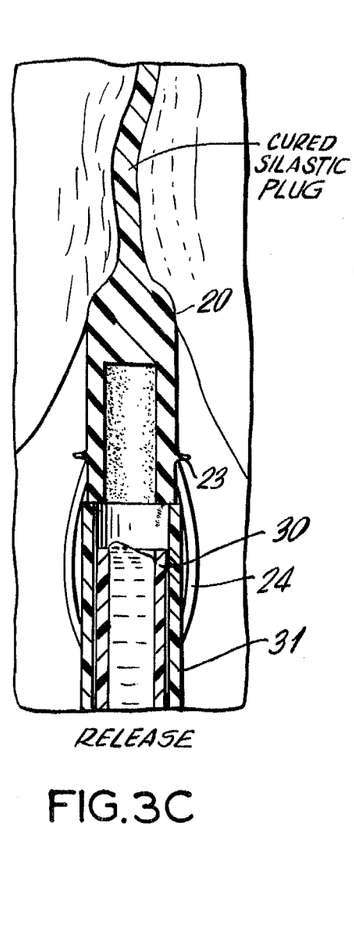
Figure 3D:
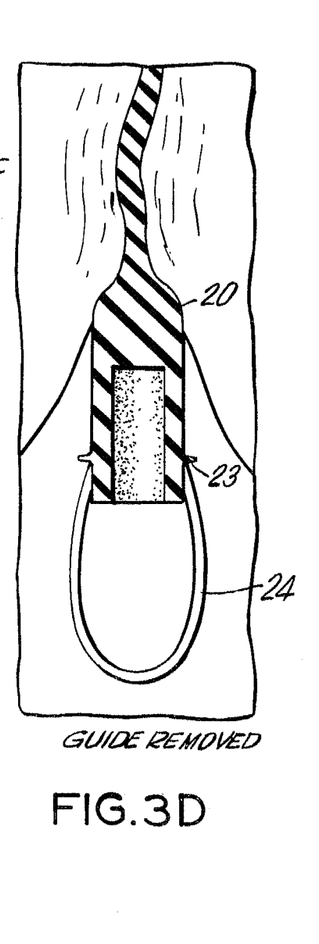
Figure 4A:
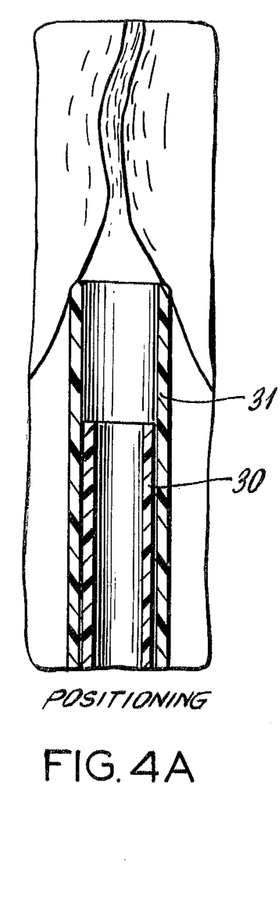
Figure 4B:
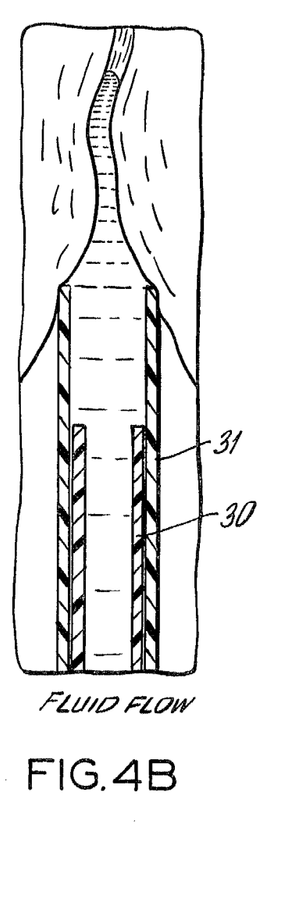
Figure 4C:
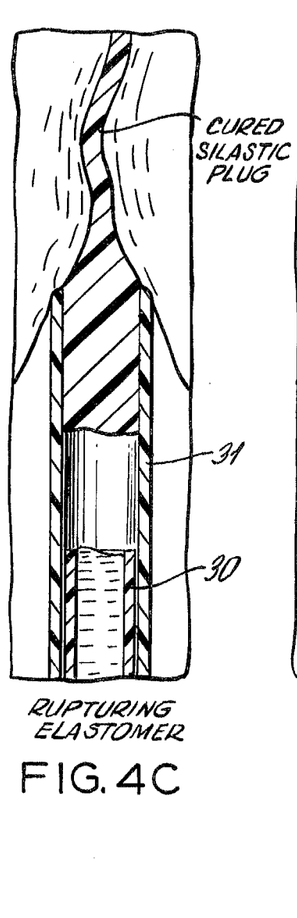
Figures 4D, 4E:
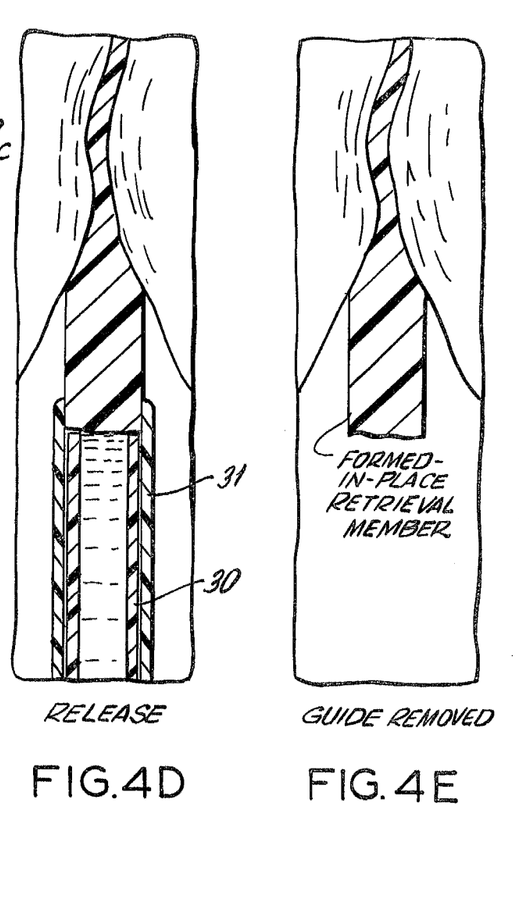

For ease in retrieving the obturating tip and integral block (formed during curing) a polyester thread 24 is imbedded as shown in FIG. 2. The thread is of a white multifilament ethylene terphthalate and is approximately .2 mm in diameter uncompressed. The thread may be coated with silicone rubber, such as air-curing medical adhesive. It may optionally take the form of a closed loop as shown for example in FIG. 3D, or be completely imbedded in an extended body version of the obturating tip (unshown). In the free loop configuration either a conventional blunt hook or grasping forceps may be inserted through the operating channel of the hysteroscope for retrieval. In the imbedded configuration, grasping forceps would be used. Since the use of blunt hooks and grasping forceps through operating channels of hysteroscopes are well-known, they are not described further.

It is a feature of this invention that the elastomeric material selected will adhere only to other silicone rubbers; not to human tissue, the flow channel tube 30, or other materials except by mechanical interlocking, in the case of porous substrate. Accordingly, since the tissue within which it will rest, namely the oviduct, is topically external (like mucous membranes), the block is mechanical rather than adhesive in nature, and the block does not cross tissue lines. Accordingly, it is believed that the body does not see it as a foreign object, and the rejection phenomenon does not come into play.

Figure 1:
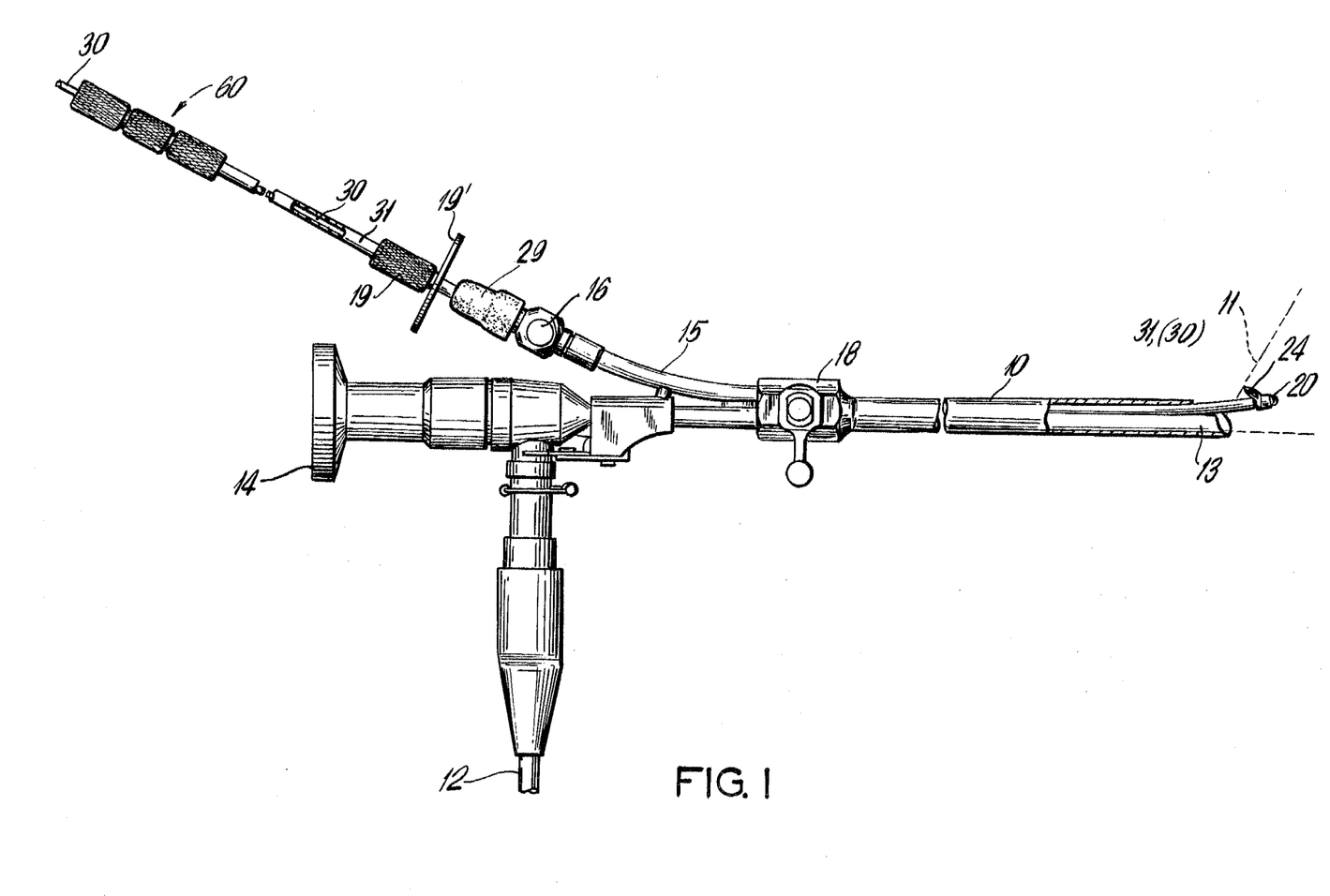
FIG. 1 is a schematic illustration of an operating hysteroscope showing the obturating tip and telescoping (concentric) tubes in position within the operating channel.

Turning now to FIG. 1, a conventional operating hysteroscope is shown having a standard operating channel 10, approximately 2.3 mm in internal diameter and approximately 30 cm in length. Compatibility with the inventive methodology has been found to be particularly demonstrated by Carl Storz, Wolf, and ACMI instruments having sheaths of 6 to 7 mm outside diameter with forward oblique viewing as shown by the dash lines at 11 and illumination from a variable intensity source (not shown) which passes through the fiberoptic illuminating tubes 12 to the hysteroscope tip 13 within which are mounted, in the conventional manner, the fiberoptic ends and the objective viewing lens. The lens carries a magnified image to the ocular lens in eye piece 14. Thus the hysteroscope permits the "cold" viewing of the uterus and the obturating tip to be located at the uterine end of the oviduct without light-heat. The hysteroscope also includes an operating channel 15 through which the flow and outer channel tubes 30 and 31 pass. Valve 18 and its accompanying fittings (not shown) permit the introduction of hysteroscope visualizing fluid into the uterus prior to insertion of the operative tubes 30, 31 carrying the obturating tip and the elastomeric material.

Figures 7, 8:
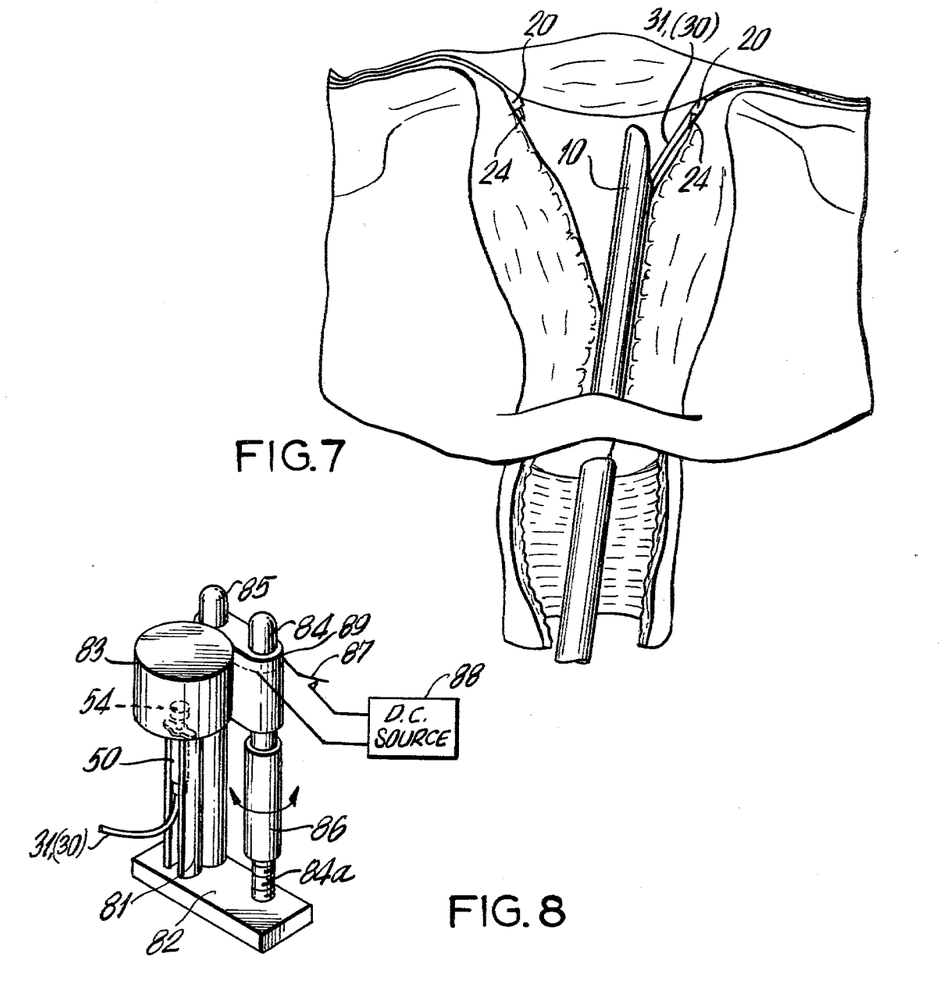
FIG. 7 illustrates schematically the hysteroscope uterus relationship during the method of the invention.
FIG. 8 illustrates an alternative arrangement for flow actuation of the elastomeric material.

The illustration of FIG. 1 displays the apparatus of the invention as it would appear just prior to the introduction of the elastomeric material in tube 30 (see also FIG. 7).

The obturator tip is positioned as previously described on inner tube 30. Pusher 19, including a thumb flange, 19' is mounted on the outer tube 31, by any conventional arrangement (such as a compression collet), to permit movement of the obturating tip (including, of course, the inner and outer tubes 30 and 31) at the oviduct end. As will be seen, pusher 19 also serves, upon curing of the elastomer, to retain the outer tube 31 in position while the inner tube was withdrawn; forcing the obturator tip's engagement with the channel tube 30 to be broken.

Prior to a detailed discussion of the methodology involved in the invention, three sub-systems will be discussed in detail. These include the mixer and dispenser for thoroughly and quickly mixing the catalyst with the fluid elastomer-precursor; the tubing 30 and 31; and the system for the flow actuation of the catalyzed fluid elastomeric material.

Because the resultant cured elastomer will be relatively rubber-like in consistency, and because the oviducts are extremely narrow (of the order of magnitude of 1 mm) it is important that no air bubbles be occluded in the catalyzed elastomer. Accordingly, a non-air-entraining mixer and dispenser has been developed to assure against such an event. The mixer-dispenser shown in FIG. 5 includes a cylindrical body 50 into which a reciprocating plunger assembler 52 is mounted. The delivery end of the mixer-dispenser has a luer fitting 51 as do most of the connections for the system. A luer fitting is a commercially available quick connect and utilizes helical threads to interlock hermetically, male and female mating cones. In FIG. 5 a luer end-cap hermetically seals the mixer-dispenser end.

The fluid elastomer-precursor material is poured into the cylinder 50 before insertion of the plunger assembly 52 which is a friction fit within cylinder 50. This is followed by degassing in a vacuum chamber with an overflow funnel on the luer fitting 51, and then by capping. At the time of use, the catalyst (about 1.4% concentration by weight) is injected through the luer fitting end and the end cap replaced. When the plunger assembly is seated in the cylinder 50, it is hermetically sealed by virtue of the pair of o-rings 53 with the lower-most o-ring functioning as an inner seal, and the upper-most functioning as an outer seal. Mixing is accomplished by reciprocating the cap 54 relative the knurled grip 55 (spring 56 acts as a constant return). The reciprocation causes the mixing head 57 mounted upon shaft 58 to thoroughly and quickly mix the catalyst and fluid elastomer precursor. Since there is no air in the system, none can be entrained. FIG. 5A is a detail of the mixing head. The mixing is accomplished by the action of the flanges 57' and channels 57" the relationship or ratio of cross-sections of which depend on the mixture viscosity. Approximately 50/50 has been found suitable.

Mixing should be accomplished as expeditiously as possible with a quarter turn rotation of cap 54 (and hence the mixing head) at the end of each double stroke. Approximately 30 seconds of mixing will suffice for the described elastomer materials. Upon completion of the mixing, the mixing head 57 is withdrawn to the locking pin 59 and by a 90° rotation locked in position; the entire assembly thereupon acts as a normal syringe for injection of the materials through the luer fitting (upon removal of the end cap 51'). With the described apparatus of FIG. 5 it is possible to thoroughly mix the constituents without air-entrainment and then convert the arrangement to a dispenser by the simple locking of the mixing head to the plunger piston assembly. The mixer dispenser should have a volume of approximately 3 cc's, preferably a polypropylene barrel and the internal parts; mixing head, shaft locking pin and shaft cap of stainless steel.

Tubing 30 and 31 are of an inert, resilient, flexible thermoplastic preferably transparent for reasons that will be discussed. An exemplary material has been found to be medical grade polysulfone, extruded in continuous lengths. The inner tube which carries the elastomer is approximately 1 mm I.D. and 1½ mm O.D., whereas preferable dimensions for the outer tube is 1.6 mm I.D. with an O.D. of approximately 2 mm. Alternatively the tubes may be made from polyphenylsulfone, polycarbonate, polytetrafluoreothylene, fluorinated ethylene-propylene copolymer, polypropylene and thermoplastic polyester.

Polysulfone is ideal in that it is steamed sterilizable and transparent, having a good combination of high tensile strength and the desired flexibility. Further, it may be heat treated and mechanically stressed to induce an approximate 50 cm radius of curvature. This curvature helps permit the obturating tip to directly address the oviducts in full view of the subjective lens of the hysteroscope, see FIG. 7.

The inner and outer polysulfone tubes 30 and 31 respectively are held in fixed relation to each other by means of a double-ended collet 60 (FIG. 1), the right-hand side of which frictionally grasps the outer tube 31 which is dead-ended in between the collets and the left-hand portion of which frictionally engages the inner tube 30. Until unlocked, as will be described later, the inner and outer tubes 30 and 31 (because of the double-ended collet) act as a unit.

Figure 6:
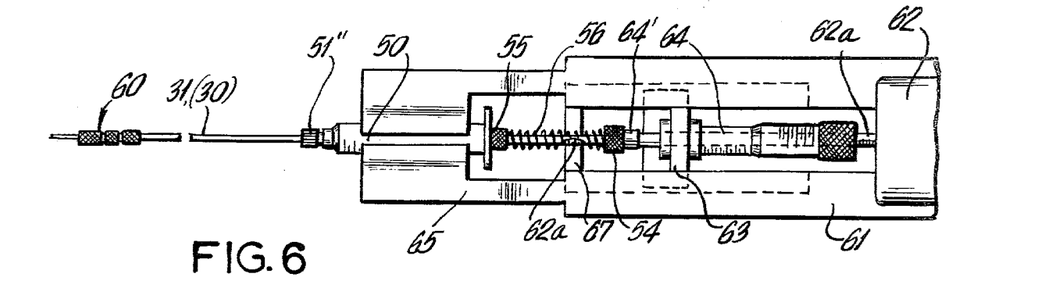
FIG. 6 is a schematic illustration of the apparatus for flow actuation of the catalyzed, but yet uncured elastomeric material.

FIG. 6 describes the arrangement for the flow actuation of the catalyzed elastomer-precursor material. Mounted upon an extruded aluminum track 61 is a variable speed, torque-independent motor 62 driving an advancing screw 62a. The other end of advancing screw 62a is journalled in crossmember 67 for rigidity. Riding within the track 61 is carriage 63 which is coupled to screw 62a for advancement under control of the motor 62. Fixedly carried on the carriage is a micrometer 64; the adjustable tip 64' of which abuts the end cap 54 of the mixer-dispenser 50. The mixer-dispenser itself is fixedly mounted in relation to the aluminum track by means of, for example, a pressure fit connecting member 65.

As will be apparent from the foregoing description, initiation of the motor 62 turns the advancing screw 62a and advances carriage 63 to the left, forcing the micrometer 64 to move the piston to the mixer-dispenser 50 into engagement with the elastomeric material and thereby forcing the catalyzed material through luer fitting 51" and the inner tube 30. Micrometer 64 is included to permit tactile adjustments during use, and for presetting the abutment between the micrometer end 64' and mixer-dispenser end cap 54. If desired, a resettable digital counter may be included to measure turns of the screw drive and thereby give a more precise indication of the amount of fluid being dispensed.

Because the primary object of the flow actuation device is to provide a constant pressure upon the catalyzed elastomer-precursor material, which pressure may not exceed certain uterine and apparatus criteria, the flow actuation device is capable of simplification, and one such simplified arrangement is shown in FIG. 8. In this arrangement the mixer-dispenser 50 is retained within a support stand 81 resting upon a platform 82. Weight 83 abuts the end cap 54 of the mixer-dispenser and rides uprights 84 and 85 (preferably on linear ball bearings). Upright 84 includes a screw thread 85 thereon and an adjustable stop 86 riding the thread for controlling the sliding mass of weight 83. The adjustable stop 86 serves the multi-function of starting, stopping and becoming a rest for weight 83 bearing upon the piston of the mixer-dispenser 50. A micrometer may be included (not shown) through the center of weight 83 similarly as in FIG. 6 for precise adjustments.

Alternatively, or in conjunction, the arrangement may include an electric toroid 89 would about one or both of the uprights 84 and 85; the uprights being made of para-magnetic material. The toroid would be normally energized, through normally closed switch 87, by source 88, thereby retaining the weight 83 in any vertical position. Switch 87 may be foot-actuated to interrupt the circuit and permit the weight to bear upon the end cap 54. Release of the actuation would again energize the circuit and halt the progress of the weight.

We turn now to the methodology of the invention.

The patient is prepared for hysteroscopic examination using standard medical procedures and local anesthesia (cervical block). The air inside the hysteroscope sheath is replaced with a hysteroscopy fluid; for example, 32% dextran 70 in 10% glucose; prior to the insertion of the instrument into the cervical canal. This is accomplished by closing valve 16 and opening valve 18 upon which there is a fitting (not shown) to which the hysteroscopy fluid dispenser, using normal fittings is attached. The hysteroscope is now inserted into the cervical canal and the hysteroscopy fluid pressurized (below 150 mm Hg) inflating the uterus for the procedure which will follow. The arrangement of FIG. 8 (with a 50 cc syringe substituted for the mixer-dispenser 50) may be employed for this purpose. The introduction of hysteroscopy fluid provides an interface with the objective lens permitting clear and relatively unimpeded, visualization of the uterus.

It is a feature of this invention that the obturating hysteroscope may be employed to identify the sometimes hard to find tubal ostium. This is accomplished by injecting a small quantity of 0.01% methylene blue in normal saline into the flow channel 30. This saline solution is of lower viscosity than the hysteroscopy fluid and I have found it forms "rivers" which flow toward the oviduct lumen of interest. This flow positively identifies the tubal ostium.

The obturating tip is now firmly positioned in the tubal ostium by pusher 19, in order to achieve a moderate sealing force. At this point the mixer-dispenser which already contains the elastomer material less catalyst, has added thereto the stannous octoate catalyst. This is preferably accomplished using a gas-tight syringe with the tip of the needle placed approximately half way into the mass within the mixer-dispenser, through the luer fitting end.

The shaft of the mixer-dispenser is then reciprocated to thoroughly mix the ingredients (the luer tip is capped). After mixing, head 54 is locked into dispenser position with a 90° twist in the counter-clockwise direction (as seen from the end cap); the luer cap is removed and a small quantity of the catalyzed mixture is injected onto a glass plate. This provides an external sample on which the curing can be gauged and simultaneously discharges any poorly catalyzed material inside the dead space in the luer tip. The mixer-dispenser is now fitted to the end of tube 30 emanating from the double-ended collet 60 and is placed into the holder of the flow actuating system as shown in FIG. 6. The micrometer is adjusted until its head 64' contacts shaft cap 54.

The motor of the flow actuating system is activated and the flow interface between the colored saline solution and catalyzed mixture watched for free forward motion.

Simultaneously by watching on the eye piece 14 of the hysteroscope, the catalyzed mixture can be observed replacing the colored fluid and the flow in the transparent tubes 30 and 31 can be watched. Any indications of back flow of the colored saline into the uterine cavity may be eliminated by increasing the finger force on pusher 19.

Meanwhile when it is observed that the catalyzed mixture interface has just disappeared into the operating channel of the hysteroscope, the motor speed may be reduced by approximately 75% until the interface comes into hysteroscopic view from the eye piece 14. When it does so, the motor is shut off and the normal pressure in the system will result in coasting.

At this point, and turning now to FIG. 3, the obturator tip is positioned as shown in detail A. As the coasting proceeds, the fluid flow will appear as shown in FIG. 3B. After some empirical experimentation the speed of the motor can be adjusted so that the liquid coasting fully fills the oviduct, i.e., fills the oviduct sufficiently so that the curing elastomeric material exists on both sides of the isthmus of the fallopian tube (narrow portion) and thereby when cured will be mechanically locked in the oviduct.

After approximately 2½ minutes from completion of mixing, gelling will be evident in the external sample and all flow will have ceased through the transparent flow tubes 30 and 31. The obturator tip is maintained firmly in contact with the tubal ostium for approximately another minute and a half at which time the external sample will show a snappy elastic behavior (obviously as different levels of catalyst are used, the observed behavior of the sample, as well as the time involved in the procedure will vary). At this time the left collet of member 60 is loosened and tubes 30 and 31 are rendered independent of one another. Pusher 19 is held now in position and the inner tube 30 is slid back until its distal end can just be seen outside the operating channel. This snaps the cured elastomer at the end of the flow tube as shown in FIG. 3C. The outer tube is now withdrawn from the operating channel and the operating channel valve 16 is closed. The cured elastomer, with its retrievable loop 24 and obturating tip 20, all now integral, will appear as shown in FIG. 3D. The procedure is now repeated for the other oviduct, using new tubes and a second mixer-dispenser.

After the technique is reiterated for the other tubal ostium, a flat x-ray plate is taken to confirm bilateral installation of plugs of suitable length.

FIG. 4 shows an alternate embodiment in which an obturator tip is not utilized, but rather the tip is formed in place. Under this arrangement the inner tube 30 is withdrawn after curing, rupturing the elastomeric material as shown in FIG. 4C. The inner tube is then brought back in contact so that the outer tube may be withdrawn against it as shown in FIG. 4D. Once the tubes are co-extensive as shown through the eye piece of the hysteroscope, both tubes are removed, leaving a formed inplace retrievel member as shown in FIG. 4E.

Should at a later date it be desired that the contraceptive device be removed, a hysteroscope of the type shown in FIG. 1 may be employed to expand the uterus, using hysteroscopic fluid as described and a conventional grasping forceps or blunt edge hook inserted in the operating channel (the latter where a retrieval thread is employed) to remove the plug.

Removal is affected by a principal similar to that normally encountered with a rubber band. Because the volume of a rubber band remains constant upon stretching, the diameter necessarily decreases. The same occurs with the plug or block of the invention; the decreased diameter separates the block from the walls of the oviduct and permits removal with only a slight force.

It will be appreciated by those skilled in the art that the described and other modifications may be made in the embodiments of the invention herein-above specifically disclosed, all without departing from the spirit and scope of the invention.

I claim:

1. An apparatus for non-surgically occluding an oviduct with formed in-place elastomeric plugs comprising in combination: a hysteroscope of the type having an operating channel, a pair of substantially co-extensive flexible plastic telescoping tubes dimensioned for insertion through said operating channel, one of said tubes being an inner tube for conveying a fluid catalyzed elastomer-precursor material and the other of said tubes being an outer tube for cooperating with said inner tube; means for dispensing fluid catalyzed elastomer-precursor material through said inner tube under pre-determined pressure; means mounted externally of said hysteroscope for releasably maintaining said inner and outer tubes in a fixed relationship one to the other whereby upon the release of said maintaining means said inner and outer tubes may be moved relative to one another thereby to effect release of said plug.

2. The apparatus claimed in claim 1, wherein one of said inner and outer tube includes an end surface adapted to release a formed in-place plug.

3. The apparatus claimed in claim 1 further comprising an obturating tip mounted on one extreme end of said inner tube; said obturating tip including a channel therein through which said fluid catalyzed elastomer-precursor material passes to an oviduct.

4. The apparatus claimed in claim 3 wherein said obturating tip is friction mounted on said end.

5. The apparatus claimed in claim 3 in which said obturating tip includes conformation means for mechanically interlocking to elastomeric material curing therein.

6. The apparatus claimed in claim 5 in which the obturating tip is formed of molded elastomer, bondable to the cured elastomeric material of said plug.

7. The apparatus claimed in claim 3 in which said obturating tip further includes a loop thereon for subsequent plug retrieval.

8. The apparatus claimed in claim 1 in which the inner and outer tube material is selected from a group consisting of polysulfone, polyphenylsulfone, polycarbonate, polytetrafluorethylene, fluorinated ethylene-propylene copolymer, polypropylene and thermoplastic polyester.

9. The apparatus claimed in claim 1 in which said means for dispensing fluid catalyzed elastomer-precursor material comprises piston means for urging said elastomer-precursor material through said inner tube and means for controlling said piston means to permit a pre-determined amount of said elastomer-precursor material to pass through said inner tube.

10. The apparatus claimed in claim 9 in which said dispensing means doubles as a non-air-entraining mixer, said piston means comprising a mixing head, and means for activating said mixing head.

11. The apparatus claimed in claim 9 in which said control means comprises a variable-speed, torque-independent drive-screw means and means coupled to said drive-screw means for bearing upon said piston means.

12. The apparatus claimed in claim 9 in which said control means comprise a force normally bearing upon said piston means and means for controlling the said force.

13. The apparatus claimed in claim 12 in which said force is a weight and said means for controlling said force comprises means for halting the downward progress of said weight, the said piston means underlying said weight.

14. The apparatus claimed in claim 13 in which said downward progress controlling means comprises an electromagnet and means coupled to said electromagnet for the energizing thereof.

15. The apparatus claimed in claim 1 in which the elastomer-precursor is selected from the group consisting of poly (dimethyl siloxane) and silphenylene polymer.

16. The apparatus claimed in claim 1 in which said tubes are of transparent thermoplastic material.

17. The apparatus claimed in claim 1 in which said inner and outer tubes are curved.

18. The method for non-surgically occluding an oviduct comprising the steps of hysteroscopically locating the uterine end of an oviduct; inserting a pair of inner and outer co-extensive telescoping flexible plastic tubes, releasably maintained in fixed relative position one to the other, through the operating channel of the hysteroscope and positioning said tubes about the oviduct opening in sealing relationship thereto, the releasing means remaining external of said hysteroscope; dispensing a predetermined amount of curable elastomer-precursor into said oviduct through the inner of said tubes, permitting said elastomer-precursor to cure in situ; releasing said inner and outer tubes one from the other and moving one relative to the other to thereby break the cured elastomer; and withdrawing said hysteroscope tubes.

19. The method claimed in claim 18 wherein the step of dispensing a pre-determined amount of elastomer-precursor into said oviduct comprises the step of injecting said curable elastomer-precursor through co-extensive transparent tubes.

20. The apparatus claimed in claim 18 in which the elastomer-precursor is selected from the group consisting of poly (dimethyl siloxane) and silphenylene polymer.

21. The method claimed in claim 18 in which the step of hysteroscopically locating the uterine end of the oviduct comprises the steps of pressurizing the uterine cavity with a transparent fluid; dispensing a minor amount of colored medium into the uterus proximate the uterine end of the oviduct; and hysteroscopically observing the color drift into the oviduct.

22. The method claimed in claim 18 in which the pre-determined amount of curable elastomer-precursor dispensed into said oviduct is at least sufficient to carry the advancing face of curable elastomer-precursor beyond the isthmus of fallopia in the oviduct.

23. The method of forming an oviduct block comprising the steps of: passing an operating hysteroscope through the cervical canal; pressuring the uterine cavity with a transparent fluid; hysteroscopically locating the oviduct within the uterine cavity; inserting a pair of telescoping flexible plastic transparent tubes releasably maintained in position one relative the other through the operating channel of the hysteroscope and locating the end of said tubes about the oviduct opening in sealing relation thereto; dispensing a curable elastomer-precursor material through the inner of said tubes until the face of the advancing elastomer-precursor passes at least through the isthmus of fallopia; permitting the elastomer to cure in situ; releasing said tubes and moving the inner and outer tubes with respect to one another to thereby snap the cured elastomer near the end of the inner tube; and withdrawing the hysteroscope and tubes.

24. The method claimed in claim 23 in which said inner tube has located at the end thereof an obturating tip bondable to cured elastomeric material; the elastomer-snapping step comprising the step of withdrawing the inner tube slightly while holding the outer tube against the said obturating tip whereby the cured elastomer is snapped near the end of the inner tube and the obturating tip is released.

25. The method claimed in claim 24 in which the elastomer material includes a radiopaque substance and in which said method further comprises a final step of x-raying the oviduct(s) to determine the position of the oviduct block.

26. The method claimed in claim 23 in which the step of hysteroscopically locating the uterine end of the oviduct comprises the step of pressurizing the uterine cavity with a transparent fluid; dispensing a minor amount of colored medium into the uterus proximate the uterine end of the oviduct; and hysteroscopically observing the color drift into the oviduct.

* * * * *